US011944704B2

(12) United States Patent
McConville et al.

(10) Patent No.: US 11,944,704 B2
(45) Date of Patent: Apr. 2, 2024

(54) COENZYME Q10 AEROSOL

(71) Applicant: UNM Rainforest Innovations, Albuquerque, NM (US)

(72) Inventors: Jason Thomas McConville, Albuquerque, NM (US); Thiago Cardoso Carvalho, North Brunswick, NJ (US); Kristina Schonhoff, Bonn (DE)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 17/306,126

(22) Filed: May 3, 2021

(65) Prior Publication Data

US 2021/0267884 A1    Sep. 2, 2021

Related U.S. Application Data

(63) Continuation of application No. 16/777,594, filed on Jan. 30, 2020, now abandoned, which is a continuation of application No. 15/738,512, filed as application No. PCT/US2016/039173 on Jun. 24, 2016, now abandoned.

(60) Provisional application No. 62/185,312, filed on Jun. 26, 2015.

(51) Int. Cl.
| | |
|---|---|
| *A61K 9/00* | (2006.01) |
| *A61K 31/122* | (2006.01) |
| *A61K 47/14* | (2017.01) |
| *A61K 47/26* | (2006.01) |

(52) U.S. Cl.
CPC .......... *A61K 9/0078* (2013.01); *A61K 31/122* (2013.01); *A61K 47/14* (2013.01); *A61K 47/26* (2013.01)

(58) Field of Classification Search
None
See application file for complete search history.

(56) References Cited

U.S. PATENT DOCUMENTS

| 4,824,669 | A | 4/1989 | Folkers et al. |
|---|---|---|---|
| 5,660,835 | A | 8/1997 | Nyce |
| 7,438,903 | B2 | 10/2008 | Parkhideh |
| 7,803,366 | B2 | 9/2010 | Parkhideh |
| 8,318,898 | B2 | 11/2012 | Fasel et al. |
| 2009/0054530 | A1* | 2/2009 | Parkhideh ............ A61K 31/355 568/337 |
| 2009/0186009 | A1 | 7/2009 | Sato et al. |
| 2012/0321698 | A1 | 12/2012 | Narain et al. |
| 2014/0239525 | A1 | 8/2014 | McConville et al. |

FOREIGN PATENT DOCUMENTS

WO    WO 2009/016989 A1    2/2009

OTHER PUBLICATIONS

Balakrishnan et al. (Enhanced oral bioavailability of Coenzyme Q10 by self-emulsifying drug delivery systems, International Journal of Pharmaceutics 374 (2009) 66-72). (Year: 2009).*
Federal Institute of Industrial Property; International Search Report & Written Opinion for PCT/ US2016/039173; dated Oct. 20, 2016; 6 pages; Moscow; RU.
Shironin A. V., Fosfolipidnye nanochastitsy v. kachectve transportnoi sistemy dlya indometatsina; Avtoreferat, M., 2010; p. 1-24; especially p. 19.
Koenzim Q10; TSH "Planeta zdorovya", 2012 p. 1-6; Retrieved from the Internet; URL: http://www.fit-leader.com/ encyclopedia/coenzyme-q 10-2.shtml.
National Louis University; Solid Matter Container Coenzyme Q; Apr. 24, 2007 by Kaneka Corporation; 1 page.
Journal of Liposome Research; Development and characterization of phospholipid-stabilized submicron aqueous dispersions of coenzyme Q10 presenting continuous vibrating-mesh nebulization performance; Jun. 2013; 2 pages.
Roffe et al; Efficacy of Coenzyme Q10 for Improved Tolerability of Cancer Treatments: A Systematic Review; Journal of Clinical Oncology; vol. 22, No. 21 , Nov. 1, 2004; 7 pages.
Hsu et al; Preparation and characterization of novel coenzyme 0 10 nanoparticles engineered from microemulsion precursors; MPS PharmSciTech, Sep. 2003; 2 pages.
Siekmann et al; Preparation and Physiochemical Characterization of Aqueous Dispersions of Coenzyme 010 Nanoparticles; Pharmaceutical Research 12(2):201-8; Feb. 1995; 3 pages.

* cited by examiner

Primary Examiner — Melissa S Mercier
(74) *Attorney, Agent, or Firm* — MUETING RAASCH GROUP

(57) ABSTRACT

The present invention provides a formulation of Coenzyme Q10 that can be re-dispersed from a stable dry powder to formulation to yield a nanodispersion that can be readily aerosolized for inhalation.

16 Claims, 2 Drawing Sheets

FIG. 2B

| 2573 | Size | KSCoQ 04/19/15 Phasediagram 0.5%O 2%TC 57.5%W | Sunday, April 19, 2015 6:10:03 PM |
| 2574 | Size | KSCoQ 04/19/15 Phasediagram 0.5%O 2%TC 57.5%W | Sunday, April 19, 2015 6:12:10 PM |
| 2575 | Size | KSCoQ 04/19/15 Phasediagram 0.5%O 2%TC 57.5%W | Sunday, April 19, 2015 6:14:17 PM |
| Mean 2573-2575 | | | |
| Std Dev | | | |

| 25.1 | 91.89 | 0.213 | 114.7 | 0.000 | 0.0 | 100.0 | 0.0 | 173 |
| 25.0 | 91.87 | 0.202 | 117.4 | 0.000 | 0.0 | 100.0 | 0.0 | 173 |
| 24.9 | 91.70 | 0.219 | 176.3 | 0.000 | 0.0 | 100.0 | 0.0 | 173 |
| 25.0 | 91.82 | 0.211 | 116.1 | 0.000 | 0.0 | 100.0 | 0.0 | 173 |
| 0.1 | 0.1044 | 0.009 | 1.358 | 0.000 | 0.0 | 0.0 | 0.0 | 0.00 |

FIG. 2C

| No | Measurement from the Mean particle size ± St. Dev. Between the day water is filled in and 6 days later | Measurement from the PDI between the day water is filled in and 6 days later |
|---|---|---|
| A | 117.5±0.4619 | 0.286±0.007 |
| B | 143.0±0.6245 | 0.301±0.005 |
| C | 91.82±0.1044 | 0.211±0.009 |

COENZYME Q10 AEROSOL

RELATED APPLICATIONS

This this application is a continuation of U.S. Ser. No. 16/777,594 filed on Jan. 30, 2020, which is a continuation of U.S. Ser. No. 15/738,512 filed on Dec. 20, 2017, which is a U.S. National Phase of PCT/US2016/039173 filed on Jun. 24, 2016, which claims the benefit of U.S. Provisional Application No. 62/185,312 filed on Jun. 26, 2015, all of which are herein incorporated by reference.

BACKGROUND OF THE INVENTION

Coenzyme Q10 has a melting point around 50° C. and this makes it difficult to formulate since it is a waxy material; for example, it cannot be milled using conventional methods. Additionally, CoQ10 is degraded by heat and exposure to UV light. CoQ10 is poorly absorbed via the oral route, additionally CoQ10 has a short half-life in the body when administered via the intravenous route, this is because it is ubiquitous to the body and so is easily eliminated.

BRIEF SUMMARY OF THE INVENTION

By directly targeting the lung, a high concentration of CoQ10 can be achieved for local therapy. Additionally, absorption via the pulmonary route can provide a higher and sustained systemic concentration with one or more doses. CoQ10 is highly lipophilic and can therefore have a long residence time in the lung epithelium to provide an extended local therapeutic time.

One embodiment provides an aerosol formulation comprising coenzyme Q10. In one embodiment, the aerosol is in the form of an emulsion, including a nanoemulsion. In another embodiment, the formulation further comprises one or more carriers, one or more oils, one or more surfactants or a combination thereof.

One embodiment provides a method of treating a respiratory disease/disorder comprising administering to a subject in need of thereof an aerosol formulation discussed herein. In one embodiment, the respiratory disease/disorder is cancer. In one embodiment, the formulation is administered by aerosolization using a jet, ultrasonic, pressurized or vibrating porous plate nebulizer or other device capable of delivering the formulation to the nasal passages and/or pulmonary airway (including lung epithelium).

One embodiment provides a method of making a coenzyme Q10 (CoQ10) composition comprising dissolving CoQ10 in an oil phase together to disperse and then adding one or more surfactants to said dispersion to form an emulsion. In one embodiment, water is added to the composition after the one or more surfactants are added.

Another embodiment provides that the formulations or compositions described herein are dried (such as by freeze drying, spray drying or any other drying method). In one embodiment, the dried formulation or composition is subsequently redispersed into a formulation that can be nebulized.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIGS. 2A, 2B and 2C depict an example of an DLS result of 0.5% oil+2% surfactant+97.5% water.

DETAILED DESCRIPTION OF THE INVENTION

Figure 1:
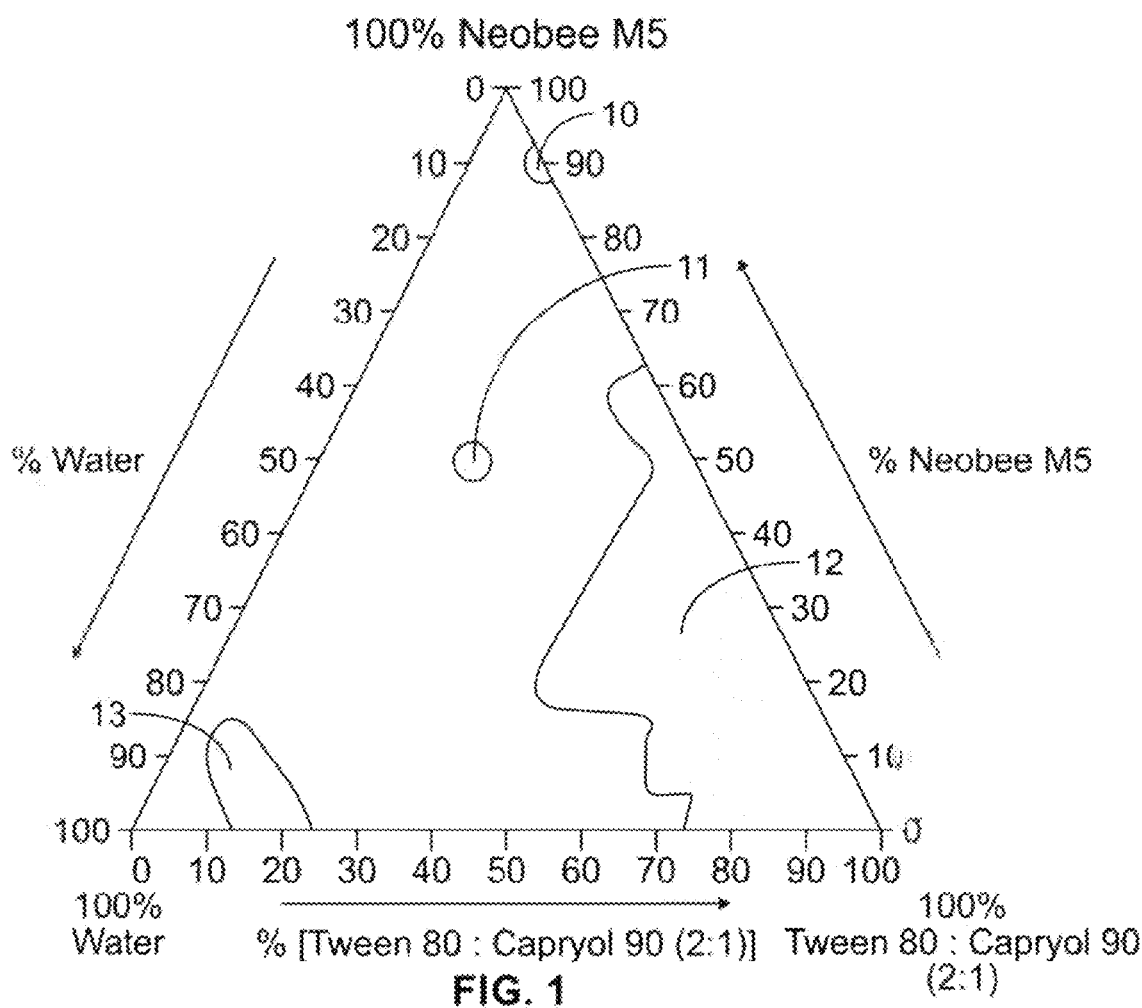
FIG. 1 provides a phase diagram within one week after making the emulsions. The shaded areas show nano-emulsion regions.
Figure 2A:
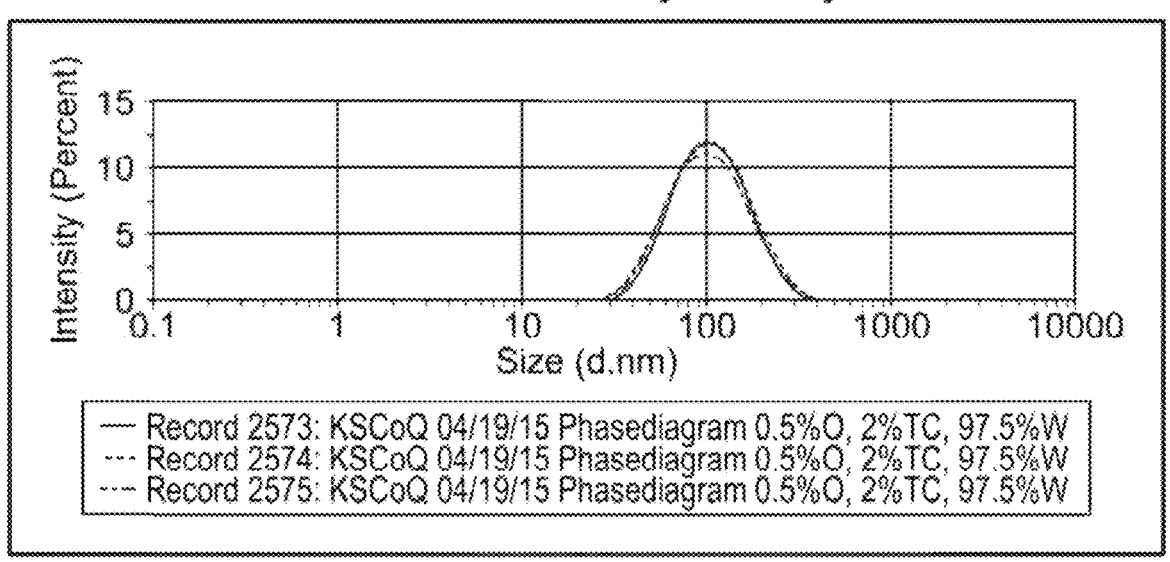

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Further, the following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment," "an embodiment," etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including," "includes," "having," "has," "with," or variants thereof, are intended to be inclusive similar to the term "comprising."

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group.

Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The terms "therapeutic agent" and "medicament" are used interchangeably herein to refer to a wide variety of substances that, when administered to an organism (human or animal), induce a desired pharmacologic or biological effect.

As use herein, the terms "administration of" and or "administering" a compound should be understood to mean providing a compound of the invention or a prodrug of a compound of the invention to a subject in need of treatment.

As used herein, "alleviating a disease or disorder symptom," means reducing the severity of the symptom or the frequency with which such a symptom is experienced by a patient, or both.

A "subject" of analysis, diagnosis, or treatment is an animal. Such animals include mammals, preferably a human. As used herein, a "subject in need thereof" is a patient, animal, mammal, or human, who will benefit from the method of this invention.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "aerosol" refers to suspension in the air. In particular, aerosol refers to the particlization or atomization of a formulation of the invention and its suspension in the air.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhalation" as used herein refers to the intake of air to the alveoli. In specific examples, intake can occur by self-administration of a medicament of the invention while inhaling through a nebulizer or other aerosol-delivery device, or by administration via a respirator, e.g., to a patient on a respirator. The term "inhalation" used with respect to a medicament of the invention is synonymous with "pulmonary administration."

The term "dispersant" as used herein refers to an agent that assists aerosolization or absorption of the medicament in lung tissue, or both. Preferably, the dispersant is pharmaceutically acceptable. As used herein, the modifier "pharmaceutically-acceptable" means approved by a regulatory agency of the federal or a state government or listed in the U.S. Pharmacopoeia or other generally recognized pharmacopoeia for use in animals, and more particularly in humans.

The terms "simultaneously," "separately" and "sequentially" as used herein refer to the administration regime of the medicament in combination with the administration of a further one or more therapeutic agent. "Simultaneously administered" refers to the medicament and one or more therapeutic agents being administered in a concomitant administration as well as separate administrations, e.g., within about one-hour, preferably within 5-10 minutes or less. "Separately administered" as used herein refers to the medicament and one or more therapeutic agents being administered independently of one another at an interval, for example at an interval of about a day to several weeks or months. The active agents may be administered in either order. "Sequentially administered" as used herein refers to administration of the medicament and one or more therapeutic agents in sequence, for example at an interval or intervals of minutes, hours, days or weeks, and if appropriate the medicament and one or more therapeutic agents may be administered in a regular repeating cycle. In all cases of "simultaneously," "separately" and "sequentially" administration, the route of administration may be the same or different.

As used herein, an "instructional material" includes a publication, a recording, a diagram, or any other medium of expression which can be used to communicate the usefulness of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified invention, or portion thereof, or be shipped together with a container which contains the invention or portion thereof. Alternatively, the instructional material may be shipped separately from the container with the intention that the instructional material and the compound be used cooperatively by the recipient.

The invention illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Coenzyme Q10 (CoQ10) is an antioxidant that is made in the human body. Coenzyme Q10, also known as ubiquinone, ubidecarenone, coenzyme Q and abbreviated at times to CoQ10, CoQ or Q10 is a 1,4-benzoquinone, where Q refers to the quinone chemical group, and 10 refers to the number of isoprenyl chemical subunits in its tail (IUPAC name 2-[(2E,6E,10E,14E,18E,22E,26E,30E,34E)-3,7,11,15,19,23,27,31,35,39-Decamethyltetraconta-2,6,10,14,18,22,26,30,34,38-decaenyl]-5,6-dimethoxy-3-methylcyclohexa-2,5-diene-1,4-dione).

This oil-soluble substance is present in eukaryotic cells, primarily in the mitochondria. It is a component of the electron transport chain and participates in aerobic cellular respiration, generating energy in the form of ATP. Ninety-five percent of the human body's energy is generated this way. Therefore, those organs with the highest energy requirements—such as the heart, liver and kidney—have the highest CoQ10 concentrations. There are three redox states of CoQ10: fully oxidized (ubiquinone), semiquinone (ubisemiquinone), and fully reduced (ubiquinol). The capacity of this molecule to exist in a completely oxidized form and a completely reduced form enables it to perform its functions in the electron transport chain, and as an antioxidant, respectively.

In one aspect, the amount of CoQ10 in the compositions and formulations described herein include about 1% to about 20% w/w, about 2% to about 15%, about 3% to about 10%, about 4% to about 8%, including about 5%, and about 6% w/w. For example, in one aspect, the amount of CoQ10 in the compositions and formulations described herein include about 0.01 g to about 0.2 g of CoQ10 per about 0.1 g to about 2.0 g of oil and/or triglyceride, including about 0.02 g to about 0.1 g CoQ10 per about 0.3 g to about 1.0 g of oil and/or triglyceride, such as about 0.03 g to about 0.06 g CoQ10 per about 0.5 gram to about 0.8 g of oil and/or triglyceride, including about 0.03 g CoQ10 per about 0.5 g of oil and/or triglyceride. One of skill will readily recognize that that amount of CoQ10 will vary depending on the amount and/or type of oil and/or triglyceride used.

FIG. 1 provides a phase diagram within one week after making the emulsions. The shaded areas 10-13 show nano-emulsion regions. In particular, for this embodiment of the present invention, area 13 identified as a region having nano-emulsions present with the base formulation components discussed above, with a suitable aqueous component.

In a preferred embodiment, maximum solubility of one drug preparation using coconut oil was found to be 6% Q10 in neobee (coconut oil).

In one embodiment, the disease or disorder is a respiratory disease selected from the group consisting of inflammatory lung disease (characterized by a high neutrophil count, e.g. asthma, cystic fibrosis, emphysema, chronic obstructive pulmonary disease/disorder or acute respiratory distress syndrome), restrictive lung disease (restrictive lung diseases are a category of respiratory disease characterized by a loss of lung compliance, causing incomplete lung expansion and increased lung stiffness, such as in infants with respiratory distress syndrome), upper respiratory tract infection (the most common upper respiratory tract infection is the common cold; however, infections of specific organs of the upper respiratory tract such as sinusitis, tonsillitis, otitis media, pharyngitis and laryngitis are also considered upper respiratory tract infections), lower respiratory tract infection (the most common lower respiratory tract infection is pneumonia, an infection of the lungs which is usually caused by bacteria, particularly *Streptococcus pneumoniae* in Western countries; worldwide, tuberculosis is a cause of pneumonia; other pathogens such as viruses and fungi can cause pneumonia for example severe acute respiratory syndrome and *pneumocystis* pneumonia; pneumonia may develop complications such as a lung abscess, a round cavity in the lung caused by the infection, or may spread to the pleural cavity), malignant tumors (malignant tumors of the respiratory system, such as small cell lung cancer, non-small cell lung cancer, adenocarcinoma of the lung, squamous cell carcinoma of the lung, large cell lung carcinoma, other lung cancers (carcinoid, Kaposi's sarcoma, melanoma), lymphoma, head and neck cancer and mesothelioma), benign tumors, pleural cavity disease, pulmonary vascular disease, neonatal diseases, bronchiolitis obliterans, chronic bronchitis, pulmonary fibrosis and/or cystic fibrosis.

In one embodiment, the disease or disorder is cancer, such as malignant tumors including malignant tumors of the respiratory system, such as small cell lung cancer, non-small cell lung cancer, adenocarcinoma of the lung, squamous cell carcinoma of the lung, large cell lung carcinoma, other lung cancers (carcinoid, Kaposi's sarcoma, melanoma), lymphoma, head and neck cancer and mesothelioma.

In addition, the formulations set for herein for the various embodiments of the present invention have many other applications. In a non-limiting example, the formulations may be used to treat cardiovascular disease.

A compound/composition of the invention can be administered by aerosol. This is accomplished by preparing an aqueous aerosol droplets, liposomal preparation, or solid particles containing the composition. A nonaqueous (e.g., fluorocarbon propellant) suspension can be used. Generally, an aqueous aerosol is made by formulating an aqueous solution or suspension of a compound of the invention together with conventional pharmaceutically acceptable carriers and stabilizers. The carriers and stabilizers can vary, but typically include nonionic surfactants (Tweens, Pluronics, sorbitan esters, Capryol, lecithin, Cremophors), pharmaceutically acceptable co-solvents such as polyethylene glycol, innocuous proteins like serum albumin, oleic acid (including fatty acids/triglycerides or their salts, including coconut oil, safflower oil, butter, cocoa butter, olive oil, and other plant/vegetable oils), amino acids such as glycine/glycerin, buffers, salts, sugars, or sugar alcohols (e.g., ethanol). Aerosols generally are prepared from isotonic solutions.

Pharmaceutical compositions of the medicament include sterile aqueous solutions (where water soluble) or dispersions and sterile powders for the extemporaneous preparation of sterile solutions or dispersions. Ideally, the composition is stable under the conditions of manufacture and storage and may include a preservative to stabilize the composition against the contaminating action of microorganisms such as bacteria and fungi. For inhalable solutions, the composition can be delivered as aerosol particles (solid or liquid) that are of respirable size: that is, particles of a size sufficiently small to pass through the mouth and larynx upon inhalation and into the bronchi and alveoli of the lungs. In general, particles ranging from about 1 to 10 microns in size (more particularly, less than about 5 microns in size) are respirable. As used herein, a particle may be a solid, a liquid droplet, and combination thereof as well as any other known dispersion unit. Compositions can be formulated to deliver the desired amount to the lungs of a subject by inhalation, or to the nasal respiratory epithelium as a topically applied liquid medicament. Liquid aerosols of respirable particles may be administered by any suitable means, such as by nebulizing a liquid composition (e.g., with a jet nebulizer or an ultrasonic nebulizer), and causing the subject to inhale the nebulized composition. Alternatively, subjects maintained on a ventilating apparatus can be administered an aerosol of respirable particles by nebulizing the liquid composition and introducing the aerosol into the inspiratory gas stream of the ventilating apparatus.

Single or multiple administrations of the pharmaceutical compositions according to the invention may be carried out. One skilled in the art would be able, by routine experimentation, to determine effective, non-toxic dosage levels of the compound and/or composition of the invention and an administration pattern which would be suitable for treating the diseases to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight. In another embodiment, an effective dosage per 24 hours may be in the range of about 2 to 15 mg per kg body weight.

Alternatively, an effective dosage may be up to about 800 mg/m$^2$. For example, generally, an effective dosage is expected to be in the range of about 25 to about 800 mg/m$^2$, 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In another embodiment, the composition of the invention is administered with one or more further therapeutic agents. In another embodiment, the medicament and the one or more further therapeutic agents are administered sequentially, simultaneously or separately.

The following example is intended to further illustrate certain particularly preferred embodiments of the invention and is not intended to limit the scope of the invention in any way.

EXAMPLE

Method

A mixture of surfactants (e.g., Tween80 and Capryo190) is made and vortexed for about 2 minutes.

The triglyceride of coconut oil was weighed in a glass vessel. It was then allowed to stand for one hour in a water bath with 37° C. along with the CoQ10, after which it was cooled down and the surfactant mixture was added. This composition was then mixed with the vortexer for about 30 seconds. After which, the composition was allowed to stand until the next day. Water was then added and it was mixed for about 1 min.

In yet another embodiment, the present provides a method for making and administering an aerosol formulation containing a desired amount of CoQ10 that is particularly useful for creating aerosol treatments having respirable compositions. In this embodiment, the emulsion is isotonic and may be made from an oil in water mixture as well as other isotonic mixtures. In a preferred embodiment, an isotonic agent is used such as dextrose, glycerin, potassium chloride, sucrose, sodium chloride, or mannitol amongst others. It has been found that isotonicity promotes the protection of the emulsion and the CoQ10 mixed therein during further processing and storage.

To further process the isotonic mixture into pellets for storage and later use, the mixture may be freeze dried. The use of an isotonic agent that is not a liquid, promotes the formation of a solid compound.

Prior to use, the mixture is re-disbursed by adding water or some other solvent and becomes isotonic again and also self-emulsifying before use as an aerosol. In addition, during re-disbursement, the tonicity of the mixture promotes shrinking of the particles in the emulsion by as much as 20% percent from their original size at the freeze drying step described above. This reduction in particle size improves use for aerosol delivery.

In another embodiment, the present invention provides a method to reduce the average particle size of the CoQ10 droplets. In this embodiment, an average reduction may be achieved wherein the droplets start at about 130 nm on average and are reduced down to about 117 nm on average, which is a 13 nm reduction in droplet size. The method may include the steps of making an aerosol formulation containing a desired amount of CoQ10 by first dissolving CoQ10 in an oil to create an oil phase. Heat may be applied and 0.03 g of CoQ10 may be added to 0.5 g of oil.

At least one surfactant is added to the oil phase. A preferred mixture ratio is 0.5 g surfactant, 0.03 g of CoQ10 and 0.5 g of oil. The mixture may also be cooled at this step.

Next water is added to create an emulsion. Preferably water is incrementally while vortexing. A preferred mixture ratio is 60 g oil, 1 g water, 0.5 g oil, 0.5 g surfactant, and 0.03 g CoQ10. At least one tonicity agent is added to the emulsion to make the emulsion isotonic. Suitable tonicity agents include, but are not limited to, dextrose, glycerin, potassium chloride, sucrose, sodium chloride, or mannitol amongst others. At this stage, the emulsion contains droplets of CoQ10 having a first average size which may be about 130 nm.

The emulsion is then freeze dried for storage and rehydrated for use. Rehydrating may be accomplished by adding water to make an isotonic emulsion. Upon rehydration, the emulsion contains droplets of CoQ10 having a second average droplet size that is less than said first average droplet size of about 117 nm. Over time, however, the droplets will increase in size. Accordingly, administration should be performed shortly after rehydration.

Methods:

Three different emulsions were prepared in accordance with the teachings of the present invention: Emulsion (1) comprised 0.03 g CoQ10 and 0.5 g triglyceride of coconut oil, both were heated together in a water bath for one hour on 37° C., and periodically shaken every 15 minutes. Following cooling to room temperature, 0.5 g polysorbate 80 was added before vortex mixing for 30 seconds using a Vortex-Genie2 mixer. After 24 hours 60 g ultrapure deionized water was added. The water was added in increased volumes and vortex mixed periodically. Finally, a 2-minute period of vortex mixing was performed to yield the final emulsion product. Emulsions (2 and 3) polysorbate 80 and Capryol 90 2:1 used instead of only polysorbate 80. In both cases 0.03 g of CoQ10 was used. For Emulsion (2) 0.5 g oil and 0.5 g surfactants were used and for Emulsion (3) 0.47 g oil and 0.96 g surfactants were used. Both Emulsions (1 and 2) were added with ultrapure deionized water to 100 mL. Finally, a 1-minute period of vortex mixing was performed to yield the final emulsion product.

For Emulsion (1) 0.08 g Sucrose with 0.17 g NaCl added. To Emulsions (2 and 3) 0.2 g Sucrose and 0.43 g NaCl added. All emulsions are freeze-dried with the FreeZone® Triad™ Freeze Dry System.

Following lyophilization each emulsion was rehydrated with ultrapure deionized water by shaking for 15 seconds.

Each emulsion product was analyzed with dynamic light scattering and the transmission electron microscopy. Aerosol particle size analysis was evaluated with using a Westech 7 cascade impactor (flowrate 15 L/min; Emulsion 1 and 2 for 7 minutes and Emulsion 3 for 8 minutes). The concentration of the impactor collection cups was measured using a validated HPLC analysis method.

Results:

For Emulsion (1) was 80.11% CoQ10 in the fine particle fraction of the USP Apparatus 6 cascade impactor, with a fine powder dose of 496.40 µg. The total emitted fraction was 72.66% with a total emitted dose of 619.60 µg.

For Emulsion (2) was the FPF 69.26%, FPD 313.64 µg, TEF 78.84% and TED 461.33 µg.

For Emulsion (3) was the FPF 84.16%, FPD 306.87 µg, TEF 78.60% and TED 331.59 µg. NGI results are shown in Table 1.

TABLE 1

USP Apparatus 6 cascade impactor results

| Emulsion | FPF [%] = Fine particle fraction (Stage 4-7) | TEF [%] = Total emmited fraction | TED [μg] = Total emitted dose | FPD [μg] = Fine powder dose |
|---|---|---|---|---|
| 1 | 80.11 | 72.66 | 619.60 | 496.40 |
| 2 | 69.26 | 78.84 | 461.33 | 313.64 |
| 3 | 84.16 | 78.60 | 331.59 | 306.87 |

The particle size of Emulsion (1) at the point without Sucrose and NaCl was 135.5±1.3 nm with a polydispersity index of 0.216±0.019 nm. After adding Sucrose and NaCl was the particle size 134.6±0.8 nm with a PDI of 0.181±0.018 nm. The final product (after lyophilization and rehydration) had a particle size of 115.7±0.9 nm and a PDI of 0.162±0.013 nm.

The particle size of Emulsion (2) without Sucrose and NaCl was 160.6±1.3 nm with a PDI of 0.229±0.008 nm. After adding Sucrose and NaCl was the particle size 161.2±1.0 nm with a PDI of 0.207±0.010 nm. The final product had a particle size of 170.6±1.1 nm and a PDI of 0.236±0.005 nm.

Emulsion (3) was the particle size without Sucrose and NaCl 95.08±0.1 nm with a PDI of 0.276±0.005 nm. After adding Sucrose and NaCl was the particle size 96.71±0.7 nm with a PDI of 0.273±0.007 nm. The final product had a particle size of 64.16±0.3 nm and a PDI of 0.205±0.007 nm. Table 2 summarizes particles size results.

TABLE 2

DLS results particle size [nm]/PDI

| Emulsion | Emulsion without Sucrose and NaCl | Emulsion with Sucrose and NaCl | Emulsion after lyophilization and rehydration |
|---|---|---|---|
| 1 | 135.5 ± 1.3/ 0.216 ± 0.019 | 134.6 ± 0.8/ 0.181 ± 0.018 | 115.7 ± 0.9/ 0.162 ± 0.013 |
| 2 | 160.6 ± 1.3/ 0.229 ± 0.008 | 161.2 ± 1.0/ 0.207 ± 0.010 | 170.6 ± 1.1/ 0.236 ± 0.005 |
| 3 | 95.08 ± 0.1/ 0.276 ± 0.005 | 96.71 ± 0.7/ 0.273 ± 0.007 | 64.16 ± 0.3/ 0.205 ± 0.007 |

Based on the above, embodiments of the present invention include the three different emulsions described above. All may be used as nebulization formulations. By using both surfactants, particle size was smaller and the FPD was higher with more surfactant and less oil. The emulsion with only polysorbate 80 yielded a 115.7 nm emulsion with a high FPF.

In yet another preferred embodiment, the particle/droplet may be on average 1 micron or less. In other preferred embodiments, particle/droplet may be on average 500 nanometers or less or 200 nanometers or less.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. An aerosol delivery system for administering coenzyme Q10 to the pulmonary tract of a subject, the system comprising an emulsion comprising:
    coenzyme Q10 (CoQ10) having an effective oil phase dispersion size of 1 micron or less;
    an aerosolizable non-ionic surfactant; and
    a tonicity agent;
    wherein a dried form of the emulsion is self-emulsifying when re-dispersed in a suitable solvent.

2. The aerosol delivery system of claim 1, wherein the tonicity agent is a solid.

3. The aerosol delivery system of claim 1, wherein the emulsion comprises one or more carriers, one or more oils, one or more surfactants, or a combination thereof, in addition to the non-ionic surfactant.

4. The aerosol delivery system of claim 1, wherein the suitable solvent comprises water.

5. The aerosol delivery system of claim 1, wherein the emulsion is aerosolized to comprise droplets comprising coenzyme Q10, wherein the droplets have an average diameter of about 117 nm.

6. The aerosol delivery system of claim 1, wherein the emulsion comprises a mixture ratio of 0.03 g of coenzyme Q10 to 0.5 g of oil.

7. A method of preparing a coenzyme Q10 formulation, the method comprising:
    preparing a first emulsion containing:
        an aerosolizable non-ionic surfactant; and
        coenzyme Q10 having an effective oil phase dispersion size of 1 micron or less;
    preparing a solid dry matrix formed from a dried state of the first emulsion;
    re-dispersing the solid dry matrix in a suitable solvent to produce an aerosolizable second emulsion; and
    aerosolizing the second emulsion.

8. The method of claim 7, wherein the solid dry matrix is prepared by freeze drying or spray drying the first emulsion.

9. A method for making an aerosol formulation containing a desired amount of CoQ10, the method comprising:
    dissolving CoQ10 in an oil to create an oil phase;
    adding at least one aerosolizable non-ionic surfactant to the oil phase;
    adding water to the oil phase to create a first emulsion;
    adding at least one tonicity agent to make the first emulsion isotonic, the first emulsion comprising droplets of CoQ10 having a first average size;
    freeze drying the first emulsion; and
    rehydrating the freeze-dried first emulsion with water to make an aerosolizable isotonic second emulsion, the second emulsion comprising droplets of CoQ10 having a second average droplet size that is less than the first average droplet size.

10. The method of claim 9, wherein the oil phase comprises CoQ10 and oil in a mixture ratio of 0.03 g of CoQ10 to 0.5 g of oil.

11. The method of claim 9, wherein the first emulsion has a mixture ratio of 60 g oil, 1 g water, 0.5 g oil, 0.5 g surfactant, and 0.03 g CoQ10.

12. The method of claim 9, wherein the second average droplet size is 117 nanometers or less.

13. The method of claim 9, wherein the second average droplet size is 64 nanometers or less.

14. A method of treating a disorder, the method comprising administering the aerosol formulation prepared by the method of claim 7 to a subject in need of thereof.

15. The method of claim 14, wherein disorder is cancer, cardiovascular disease, or obesity.

16. The method of claim 14, wherein the formulation is administered by aerosolization using a jet, ultrasonic nebulizer, pressurized nebulizer, vibrating porous plate nebulizer, or other device capable of delivering the formulation to the nasal passages and/or pulmonary airway.

* * * * *